United States Patent [19]

Barnett et al.

[11] Patent Number: 5,122,599
[45] Date of Patent: Jun. 16, 1992

[54] CDNAS CODING FOR MEMBERS OF THE CARCINOEMBRYONIC ANTIGEN FAMILY

[75] Inventors: Thomas R. Barnett, East Haven; James J. Elting, Madison; Michael E. Kamarck, Bethany, all of Conn.; Axel W. Kretschmer, Wulfrath, Fed. Rep. of Germany

[73] Assignee: Molecular Diagnostics, Inc., West Haven, Conn.

[21] Appl. No.: 274,107

[22] Filed: Nov. 21, 1988

Related U.S. Application Data

[63] Continuation-in-part of Ser. No. 207,628, Jun. 15, 1988, Pat. No. 5,001,108, which is a continuation-in-part of Ser. No. 60,031, Jun. 19, 1987, abandoned, which is a continuation-in-part of Ser. No. 16,683, Feb. 19, 1987, abandoned, which is a continuation-in-part of Ser. No. 896,361, Aug. 13, 1986, abandoned.

[51] Int. Cl.⁵ .............. C07H 15/12; C12Q 1/68; C12N 15/00
[52] U.S. Cl. .................................. 536/27; 435/6; 935/77; 935/78
[58] Field of Search ............... 536/27; 435/6; 935/77, 935/78

[56] References Cited

U.S. PATENT DOCUMENTS 4,228,236 10/1980 Jakstys et al. .................. 435/1
4,489,167 12/1984 Ochi et al. ..................... 436/518

OTHER PUBLICATIONS

Gold et al, J. Exp. Med., 121, 439–462 (1965).

Primary Examiner—Robert A. Wax
Assistant Examiner—Mindy B. Fleisher
Attorney, Agent, or Firm—Sprung Horn Kramer & Woods

[57] ABSTRACT

This invention relates to a nucleic acid comprising a base sequence which codes for a CEA family member peptide sequence or nucleic acids having a base sequence hybridizable therewith, replicable recombinant cloning vehicles having an insert comprising such nucleic acid, cells transfected, infected or injected with such cloning vehicles, polypeptides expressed by such cells, synthetic peptides derived from the coding sequence of CEA family member nucleic acids, antibody preparations specific for such polypeptides, immunoassays for detecting CEA family members using such antibody preparations and nucleic acid hybridization methods for detecting CEA family member nucleic acid sequences using a nucleic acid probe comprising the above described nucleic acid.

6 Claims, 1 Drawing Sheet

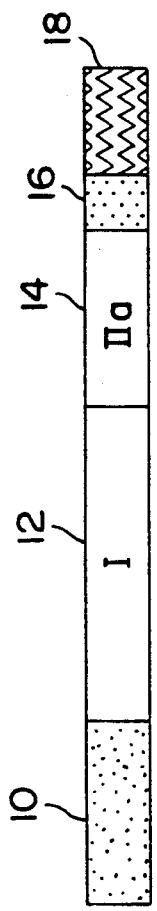
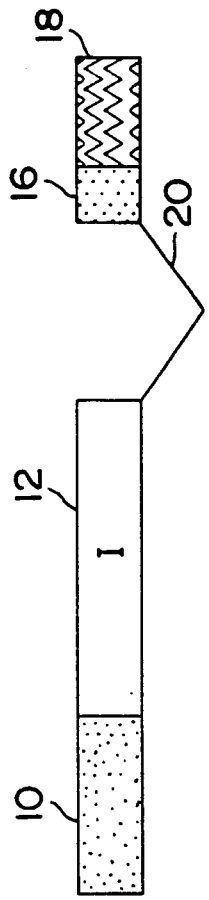
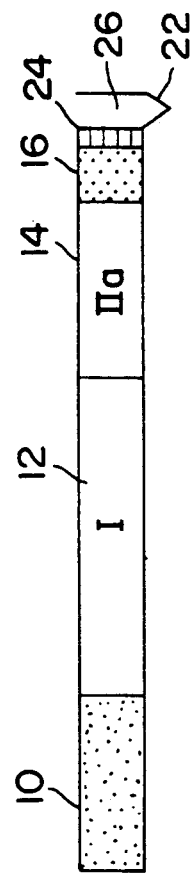
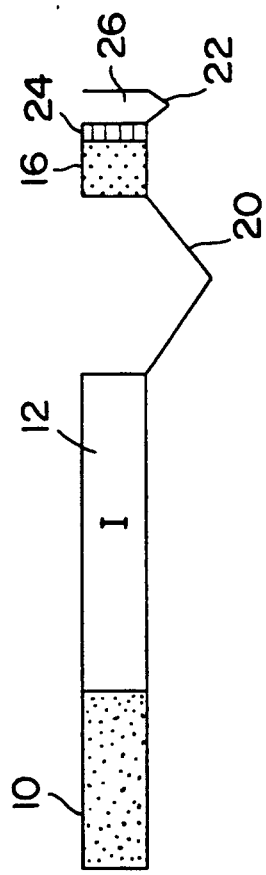
FIG.1A  TM1(CEA-(c))
FIG.1B  TM2(CEA-(e))
FIG.1C  TM3(CEA-(f))
FIG.1D  TM4(CEA-(g))

CDNAS CODING FOR MEMBERS OF THE CARCINOEMBRYONIC ANTIGEN FAMILY

CROSS-REFERENCES TO RELATED APPLICATIONS

This application is a continuation-in-part application of application Ser. No. 07/207,628, filed Jun. 15, 1988, now U.S. Pat. No. 5,001,108, which in turn is a continuation-in-part application of application Ser. No. 07/060,031, filed Jun. 19, 1987, now abandoned 6-15-90, which in turn is a continuation-in-part application of application Ser. No. 07/016,683, filed Feb. 19, 1987, now abandoned 6-15-90, which in turn is a continuation-in-part application of application Ser. No. 06/896,361, filed Aug. 13, 1986, now abandoned 4-1-91.

BACKGROUND OF THE INVENTION

1. Field of the Invention

The present invention concerns nucleic acid sequences which code for carcinoembryonic antigen (CEA) antigen family peptide sequences.

2. Background Information

Carcinoembryonic antigen was first described by Gold and Freedman, *J. Exp. Med.*, 121, 439–462, (1965). CEA is characterized as a glycoprotein of approximately 200,000 molecular weight with 50–60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do not return to normal often indicate incomplete resection of the tumor or the presence of additional tumor sites in the patient. After returning to normal levels, subsequent rapid rises in serum CEA levels usually indicate the presence of metastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such as inflammatory liver diseases and also in smokers. It is important that immunoassays used for the monitoring of cancer patient status not be interfered with by these other CEA-like antigens. Conversely, it is important to be able to distinguish the antigens by immunoassays because of the possibility that different tumor types may preferentially express different forms of CEA. If so, then the ability to reliably measure the different forms of CEA can provide the means to diagnose or more successfully treat different forms of cancer.

The members of the "CEA family" share some antigenic determinants. These common epitopes are not useful in distinguishing the members of the antigen family and antibodies recognizing them are of little use for measuring tumor-specific CEA levels.

U.S. Pat. No. 3,663,684, entitled "Carcinoembryonic Antigen and Diagnostic Method Using Radioactive Iodine", concerns purification and radioiodination of CEA for use in a RIA.

U.S. Pat. No. 3,697,638 describes that CEA is a mixture of antigens (components A and B in this case). U.S. Pat. No. 3,697,638 mentions methods for separating and radioiodinating each component and their use in specific RIA's.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labelling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-S1 and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65° to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen—After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen—Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or Tissue—for Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

| DEFINITIONS | |
|---|---|
| Nucleic Acid Abbreviations | |
| A | adenine |
| G | guanine |
| C | cytosine |
| T | thymidine |
| U | uracil |
| Amino Acid Abbreviations: | |
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous hetercyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG may be translated in three reading frames or phases, each of which affords a different amino acid sequence GCT GGT TGT AAG —Ala—Gly—Cys—Lys
G CTG GTT GTA AG —Leu—Val—Val
GC TGG TTG TAA G —Trp—Leu—(STOP).

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

cDNA Expression Vector—A procaroytic cloning vehicle which also contains sequences of nucleotides that facilitate expression of cDNA sequences in eucaroytic cells. These nucleotides include sequences that function as eucaryotic promoter, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referred to herein concerns the microinjection (use of a small syringe) of DNA into a cell.

CEA antigen family (CEA gene family)—a set of genes (gene family) and their products (antigen family) that share nucleotide sequences homologous to partial cDNA LV-7 (CEA-(a)) and as a result of theses similarities also share a subset of their antigenic epitopes. Examples of the CEA antigen family include CEA (=CEA-(b)), transmembrane CEA (TMCEA)=CEA-(c) and normal crossreacting antigen NCA (=CEA-(d)).

SUMMARY OF THE INVENTION

The present invention concerns the following DNA sequences designated as TM-2 (CEA-(e)), TM-3 (CEA-(f)), TM-4 (CEA-(g)), KGCEA1 and KGCEA2, which code for CEA antigen family peptide sequences or nucleic acids having a base sequence (DNA or RNA) that are hybridizable therewith:

SEQUENCE AND TRANSLATION OF cDNA OF TM-2

```
             10                          30                          50
CAGCCGTGCTCGAAGCGTTCCTGGAGCCCAAGCTCTCCTCCACAGGTGAAGACAGGGCCA 70                          90                         110
GCAGGAGACACCATGGGGCACCTCTCAGCCCCACTTCACAGAGTGCGTGTACCCTGGCAG
                Met Gly His Leu Ser Ala Pro Leu His Arg Val Arg Val Pro Trp Gln 130                         150                         170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                         210                         230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                         270                         290
AATCTGCCCCAGCAACTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                         330                         350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                         390                         410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp
```

SEQUENCE AND TRANSLATION OF cDNA OF TM-2
-continued

```
            430                          450                          470
ACAGGATTCTACACCCTACAAGTCATAAAGTCAGATCTTGTGAATGAAGAAGCAACTGGA
Thr Gly Phe Tyr Thr Leu Gln Val Ile  Lys Ser Asp Leu Val Asn Glu Glu Ala Thr Gly 490                          510                          530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                          570                          590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                          630                          650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                          690                          710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 690                          710
        ACTCTACTCAGTGTCACAAGGAATGACACAGGACCCTATGAGTGTGAA
            Leu Leu Ser Val Thr Arg Asn Asp Thr Gly Pro Tyr Glu Cys Glu 730                          750                          770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                          810                          830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                          870                          890
CTCTCCTGCTATGCAGCCTCTAACCCACCTGCACAGTACTCCTGGCTTATCAATGGAACA
Leu Ser Cys Tyr Ala Ala Ser Asn Pro Pro Ala Gln Tyr Ser Trp Leu Ile Asn Gly Thr 910                          930                          950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                          990                          1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                         1050                         1070
ATAGTCACTGATAATGCTCTACCACAAGAAAATGGCCTCTCACCTGGGGCCATTGCTGGC
Ile Val Thr Asp Asn Ala Leu Pro Gln Glu Asn Gly Leu Ser Pro Gly Ala Ile Ala Gly 1090                         1110                         1130
ATTGTGATTGGAGTAGTGGCCCTGGTTGCTCTGATAGCAGTAGCCCTGGCATGTTTTCTG
Ile Val Ile Gly Val Val Ala Leu Val Ala Leu Ile Ala Val Ala Leu Ala Cys Phe Leu 1150                         1170                         1190
CATTTCGGGAAGACCGGCAGGGCAAGCGACCAGCGTGATCTCACAGAGCACAAACCCTCA
His Phe Gly Lys Thr Gly Arg Ala Ser Asp Gln Arg Asp Leu Thr Glu His Lys Pro Ser 1210                         1230                         1250
GTCTCCAACCACACTCAGGACCACTCCAATGACCCACCTAACAAGATGAATGAAGTTACT
Val Ser Asn His Thr Gln Asp His Ser Asn Asp Pro Pro Asn Lys Met Asn Glu Val Thr 1270                         1290                         1310
TATTCTACCCTGAACTTTGAAGCCCAGCAACCCACACAACCAACTTCAGCCTCCCCATCC
Tyr Ser Thr Leu Asn Phe Glu Ala Gln Gln Pro Thr Gln Pro Thr Ser Ala Ser Pro Ser 1330                         1350                         1370
CTAACAGCCACAGAAATAATTTATTCAGAAGTAAAAAAGCAGTAATGAAACCTGTCCTGC
Leu Thr Ala Thr Glu Ile Ile Tyr Ser Glu Val Lys Lys Gln 1390                         1410                         1430
TCACTGCAGTGCTGATGTATTTCAAGTCTCTCACCCTCATCACTAGGAGATTCCTTTCCC
```

SEQUENCE AND TRANSLATION OF cDNA OF TM-2
-continued

```
1450                    1470                    1490
CTGTAGGGTAGAGGGGTGGGGACAGAAACAACTTTCTCCTACTCTTCCTTCCTAATAGGC 1510                    1530                    1550
ATCTCCAGGCTGCCTGGTCACTGCCCCTCTCTCAGTGTCAATAGATGAAAGTACATTGGG 1570                    1590                    1610
AGTCTGTAGGAAACCCAACCTTCTTGTCATTGAAATTTGGCAAAGCTGACTTTGGGAAAG 1630                    1650                    1670
AGGGACCAGAACTTCCCCTCCCTTCCCCTTTTCCCAACCTGGACTTGTTTTAAACTTGCC 1690                    1710                    1730
TGTTCAGAGCACTCATTCCTTCCCACCCCCAGTCCTGTCCTATCACTCTAATTCGGATTT 1750                    1770                    1790
GCCATAGCCTTGAGGTTATGTCCTTTTCCATTAAGTACATGTGCCAGGAAACAGCGAGAG 1810                    1830                    1850
AGAGAAAGTAAACGGCAGTAATGCTTCTCCTATTTCTCCAAAGCCTTGTGTGAACTAGCA 1870                    1890                    1910
AAGAGAAGAAAATCAAATATATAACCAATAGTGAAATGCCACAGGTTTGTCCACTGTCAG 1930                    1950                    1970
GGTTGTCTACCTGTAGGATCAGGGTCTAAGCACCTTGGTGCTTAGCTAGAATACCACCTA 1990                    2010                    2030
ATCCTTCTGGCAAGCCTGTCTTCAGAGAACCCACTAGAAGCAACTAGGAAAAATCACTTG 2050                    2070                    2090
CCAAAATCCAAGGCAATTCCTGATGGAAAATGCAAAAGCACATATATGTTTTAATATCTT 2110                    2130                    2150
TATGGGCTCTGTTCAAGGCAGTGCTGAGAGGGAGGGGTTATAGCTTCAGGAGGGAACCAG 2170                    2190                    2210
CTTCTGATAAACACAATCTGCTAGGAACTTGGGAAAGGAATCAGAGAGCTGCCCTTCAGC 2230                    2250                    2270
GATTATTTAAATTGTTAAAGAATACACAATTTGGGGTATTGGGATTTTTCTCCTTTTCTC 2290                    2310                    2330
TGAGACATTCCACCATTTTAATTTTTGTAACTGCTTATTTATGTGAAAAGGGTTATTTTT 2350                    2370                    2390
ACTTAGCTTAGCTATGTCAGCCAATCCGATTGCCTTAGGTGAAAGAAACCACCGAAATCC 2410                    2430                    2450
CTCAGGTCCCTTGGTCAGGAGCCTCTCAAGATTTTTTTTGTCAGAGGCTCCAAATAGAAA 2470                    2490                    2510
ATAAGAAAAGGTTTTCTTCATTCATGGCTAGAGCTAGATTTAACTCAGTTTCTAGGCACC 2530                    2550                    2570
TCAGACCAATCATCAACTACCATTCTATTCCATGTTTGCACCTGTGCATTTTCTGTTTGC 2590                    2610                    2630
CCCCATTCACTTTGTCAGGAAACCTTGGCCTCTGCTAAGGTGTATTTGGTCCTTGAGAAG 2650                    2670                    2690
TGGGAGCACCCTACAGGGACACTATCACTCATGCTGGTGGCATTGTTTACAGCTAGAAAG 2710                    2730                    2750
CTGCACTGGTGCTAATGCCCCTTGGGAAATGGGGCTGTGAGGAGGAGGATTATAACTTAG 2770                    2790                    2810
GCCTAGCCTCTTTTAACAGCCTCTGAAATTTATCTTTTCTTCTATGGGGTCTATAAATGT
```

-continued
SEQUENCE AND TRANSLATION OF cDNA OF TM-2

```
     2830                     2850                      2870
ATCTTATAATAAAAAGGAAGGACAGGAGGAAGACAGGCAAATGTACTTCTCACCCAGTCT 2890                     2910                      2930
TCTACACAGATGGAATCTCTTTGGGGCTAAGAGAAAGGTTTTATTCTATATTGCTTACCT 2950                     2970                      2990
GATCTCATGTTAGGCCTAAGAGGCTTTCTCCAGGAGGATTAGCTTGGAGTTCTCTATACT 3010                     3030                      3050
CAGGTACCTCTTTCAGGGTTTTCTAACCCTGACACGGACTGTGCATACTTTCCCTCATCC 3070                     3090                      3110
ATGCTGTGCTGTGTTATTTAATTTTTCCTGGCTAAGATCATGTCTGAATTATGTATGAAA 3130                     3150                      3170
ATTATTCTATGTTTTTATAATAAAAATAATATATCAGACATCGAAAAAAAAAA
```

SEQUENCE AND TRANSLATION OF cDNA OF TM-3

```
      10                        30                        50
CAGCCGTGCTCGAAGCGTTCCTGGAGCCCAAGCTCTCCTCCACAGGTGAAGACAGGGCCA 70                        90                       110
GCAGGAGACACCATGGGGCACCTCTCAGCCCCACTTCACAGAGTGCGTGTACCCTGGCAG
             Met Gly His Leu Ser Ala Pro Leu His Arg Val Arg Val Pro Trp Gln 130                       150                       170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                       210                       230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                       270                       290
AATCTGCCCCAGCAACTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                       330                       350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                       390                       410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                       450                       470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                       510                       530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                       570                       590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                       630                       650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly
```

-continued
SEQUENCE AND TRANSLATION OF cDNA OF TM-3

```
        670                          690                          710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                          750                          770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                          810                          830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                          870                          890
CTCTCCTGCTATGCAGCCTCTAACCCACCTGCACAGTACTCCTGGCTTATCAATGGAACA
Leu Ser Cys Tyr Ala Ala Ser Asn Pro Pro Ala Gln Tyr Ser Trp Leu Ile Asn Gly Thr 910                          930                          950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                          990                         1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                         1050                         1070
ATAGTCACTGAGCTAAGTCCAGTAGTAGCAAAGCCCCAAATCAAAGCCAGCAAGACCACA
Ile Val Thr Glu Leu Ser Pro Val Val Ala Lys Pro Gln Ile Lys Ala Ser Lys Thr Thr 1090                         1110                         1130
GTCACAGGAGATAAGGACTCTGTGAACCTGACCTGCTCCACAAATGACACTGGAATCTCC
Val Thr Gly Asp Lys Asp Ser Val Asn Leu Thr Cys Ser Thr Asn Asp Thr Gly Ile Ser 1150                         1170                         1190
ATCCGTTGGTTCTTCAAAAACCAGAGTCTCCCGTCCTCGGAGAGGATGAAGCTGTCCCAG
Ile Arg Trp Phe Phe Lys Asn Gln Ser Leu Pro Ser Ser Glu Arg Met Lys Leu Ser Gln 1210                         1230                         1250
GGCAACACCACCCTCAGCATAAACCCTGTCAAGAGGGAGGATGCTGGGACGTATTGGTGT
Gly Asn Thr Thr Leu Ser Ile Asn Pro Val Lys Arg Glu Asp Ala Gly Thr Tyr Trp Cys 1270                         1290                         1310
GAGGTCTTCAACCCAATCAGTAAGAACCAAAGCGACCCCATCATGCTGAACGTAAACTAT
Glu Val Phe Asn Pro Ile Ser Lys Asn Gln Ser Asp Pro Ile Met Leu Asn Val Asn Tyr 1330                         1350                         1370
AATGCTCTACCACAAGAAAATGGCCTCTCACCTGGGGCCATTGCTGGCATTGTGATTGGA
Asn Ala Leu Pro Gln Glu Asn Gly Leu Ser Pro Gly Ala Ile Ala Gly Ile Val Ile Gly 1390                         1410                         1430
GTAGTGGCCCTGGTTGCTCTGATAGCAGTAGCCCTGGCATGTTTTCTGCATTTCGGGAAG
Val Val Ala Leu Val Ala Leu Ile Ala Val Ala Leu Ala Cys Phe Leu His Phe Gly Lys 1450                         1470                         1490
ACCGGCAGCTCAGGACCACTCCAATGACCCACCTAACAAGATGAATGAAGTTACTTATTC
Thr Gly Ser Ser Gly Pro Leu Gln 1510                         1530                         1550
TACCCTGAACTTTGAAGCCCAGCAACCCACACAACCAACTTCAGCCTCCCCATCCCTAAC 1570                         1590                         1610
AGCCACAGAAATAATTTATTCAGAAGTAAAAAAGCAGTAATGAAACCTGAAAAAAAAAAA
```

-continued
SEQUENCE AND TRANSLATION OF cDNA OF TM-3

1630

AAAAAAAAAA

SEQUENCE AND TRANSLATION OF cDNA OF TM-4

```
          10                        30                        50
CAGCCGTGCTCGAAGCGTTCCTGGAGCCCAAGCTCTCCTCCACAGGTGAAGACAGGGCCA 70                        90                       110
GCAGGAGACACCATGGGGCACCTCTCAGCCCCACTTCACAGAGTGCGTGTACCCTGGCAG
                  Met Gly His Leu Ser Ala Pro Leu His Arg Val Arg Val Pro Trp Gln 130                       150                       170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                       210                       230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                       270                       290
AATCTGCCCCAGCAACTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                       330                       350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                       390                       410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                       450                       470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                       510                       530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                       570                       590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                       630                       650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                       690                       710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                       750                       770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                       810                       830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                       870                       890
CTCTCCTGCTATGCAGCCTCTAACCCACCTGCACAGTACTCCTGGCTTATCAATGGAACA
Leu Ser Cys Tyr Ala Ala Ser Asn Pro Pro Ala Gln Tyr Ser Trp Leu Ile Asn Gly Thr
```

-continued
SEQUENCE AND TRANSLATION OF cDNA OF TM-4

```
       910                           930                           950
         .                             .                             .
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                           990                          1010
         .                             .                             .
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                          1050                          1070
         .                             .                             .
ATAGTCACTGATAATGCTCTACCACAAGAAAATGGCCTCTCACCTGGGGCCATTGCTGGC
Ile Val Thr Asp Asn Ala Leu Pro Gln Glu Asn Gly Leu Ser Pro Gly Ala Ile Ala Gly 1090                          1110                          1130
         .                             .                             .
ATTGTGATTGGAGTAGTGGCCCTGGTTGCTCTGATAGCAGTAGCCCTGGCATGTTTTCTG
Ile Val Ile Gly Val Val Ala Leu Val Ala Leu Ile Ala Val Ala Leu Ala Cys Phe Leu 1150                          1170                          1190
         .                             .                             .
CATTTCGGGAAGACCGGCAGCTCAGGACCACTCCAATGACCCACCTAACAAGATGAATGA
His Phe Gly Lys Thr Gly Ser Ser Gly Pro Leu Gln 1210                          1230                          1250
         .                             .                             .
AGTTACTTATTCTACCCTGAACTTTGAAGCCCAGCAACCCACACAACCAACTTCAGCCTC 1270                          1290                          1310
         .                             .                             .
CCCATCCCTAACAGCCACAGAAATAATTTATTCAGAAGTAAAAAAGCAGTAATGAAACCT

1330
         .
GAAAAAAAAAAAAAAAAAA
```

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a CEA, as well as labelled forms of the polypeptide. The invention also relates to polypeptides having an amino acid sequence, i.e., synthetic peptides, or the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amino acids of the aforesaid expression product.

The invention further relates to an antibody preparation specific for the above described polypeptide.

Another aspect of the invention concerns an immunoassay method for detecting CEA or a functional equivalent thereof in a test sample comprising (a) contacting the sample with the above described antibody preparation, and (b) determining binding thereof to CEA in the sample.

The invention also is directed to a nucleic acid hybridization method for detecting a CEA or a related nucleic acid (DNA or RNA) sample in a test sample comprising (a) contacting the test sample with a nucleic acid probe comprising a nucleic acid, which comprises a base sequence which codes for a CEA peptide sequence or a base sequence that is hybridizable therewith, and (b) determining the formation of the resultant hybridized probe.

The present invention also concerns a method for detecting the presence of carcinoembryonic antigen or a functional equivalent thereof in an animal or human patient in vivo comprising a) introducing into said patient a labeled (e.g., a radio-opaque material that can be detected by x-rays, radiolabeled or labeled with paramagnetic materials that can be detected by NMR) antibody preparation according to the present invention and b) detecting the presence of such antibody preparation in the patient by detecting the label.

In another aspect, the present invention relates to the use of an antibody preparation according to the present invention for therapeutic purposes, namely, attaching to an antibody preparation radionuclides, toxins or other biological effectors to form a complex and introducing an effective amount of such complex into an animal or human patient, e.g., by injection or orally. The antibody complex would attach to CEA in a patient and the radionuclide, toxin or other biological effector would serve to destroy the CEA expressing cell.

BRIEF DESCRIPTION OF THE DRAWINGS

FIG. 1 is a schematic representation of the transmembrane CEA's.

FIG. 1A is a schematic representation of TM1 (CEA-(c)).

FIG. 1B is a schematic representation of TM2 (CEA-(e)).

FIG. 1C is a schematic representation of TM3 (CEA-(F)).

FIG. 1D is a schematic representation of TM4 (CEA-(G)).

DETAILED DESCRIPTION OF THE INVENTION

In parent applications, applicants described the following CEA's:

|  |  | ATCC No |
|---|---|---|
| CEA-(a) | partial CEA (pcLV7) |  |
| CEA-(b) | full coding CEA (pc 15LV7) | 67709 |
| CEA-(c) | TM-1 (FL-CEA; pc 19-22) | 67710 |
| CEA-(d) | NCA (pcBT 20) | 67711 |

In the present application, applicants described the following CEA's:

|  |  | ATTC No |
|---|---|---|
| CEA-(e) | TM-2 (pc E22) | 67712 |
| CEA-(f) | TM-3 (pc HT-6) | 67708 |
| CEA-(g) | TM-4 |  |

ATCC Nos. 67708, 67709, 67710, 67711 and 67712 were all deposited with the American Type Culture Collection on May 25, 1988.

The sequences for CEA-(a), CEA-(b), CEA-(c) and CEA-(d) are given hereinbelow:

CEA-(a):

GG GGT TTA CAC AAC CAC CAC CCC ATC AAA CCC TTC ATC ACC AGC AAC AAC TCC AAC CCC GTG
GAG GAT GAG GAT GCT GTA GCC TTA ACC TGT GAA CCT GAG ATT CAG AAC ACA ACC TAC CTG
TGG TGG GTA AAT AAT CAG AGC CTC CCG GTC AGT CCC AGG CTG CAG CTG TCC AAT GAC AAC
AGG ACC CTC ACT CTA CTC AGT GTC ACA AGG AAT GAT GTA GGA CCC TAT GAG TGT GGA ATC
CAG AAC GAA TTA AGT GTT GAC CAC AGC GAC CCA GTC ACC CAG CGA TTC CTC TAT GGC CCA
GAC GAC CCC ACC ATT TCC CCC TCA TAC ACC TAT TAC CGT CCA GGG GTG GAA CCT CAG CCT
CTC TGC CAT GCA GCC TCT AAC CCA CCT GCA CAG TAT TCT TGG CTG ATT GAT GGG ACC GTC
CAG CAA CAC ACA CAA GAG CTC TTT ATC TCC AAC ATC ACT GAG AAG AAC AGC GGA CTC TAT
ACC TGC CAG GCC AAT AAC TCA GCC AGT GGC ACA GCA GGA CTA CAG TCA AGA CAA TCA CAG
TCT CTG CGG ATG CCC AAG CCC TCC ATC TCC AGC AAC AAC TCC AAA CCC GTG GAG GAC AAG
GAT CGC TGT GGC CTT CAC TGT GAA CCT GAG GCT CAG AAC ACA ACC TAC CTG TGG TGG GTA
AAT GGT CAG AGC CTC CCA GTC AGT CCC AGG CTG CAG CTG TCC AAT GGC AAC AGG ACC CTC
ACT CTA TTC AAT GTC ACA AGA AAT GAC GCA AGA GCC TAT GTA TGT GGA ATC CAG AAC TCA
GTG AGT GCA AAC CGC AGT GAC CCA GTC ACC CTG GAT GTC CTC TAT GCG CCG GAC ACC CCC
ATC ATT TCC CCC CCC CC

CEA-(b):

```
            10                         30                         50
CACCATGGAGTCTCCCTCGGCCCCTCCCCACAGATGGTGCATCCCCTGGCAGAGGCTCCTG
    Met Glu Ser Pro Ser Ala Pro Pro His Arg Trp Cys Ile Pro Trp Gln Arg Leu Leu 70                         90                        110
CTCACAGCCTCACTTCTAACCTTCTGGAACCCGCCCACCACTGCCAAGCTCACTATTGAA
 Leu Thr Ala Ser Leu Leu Thr Phe Trp Asn Pro Pro Thr Thr Ala Lys Leu Thr Ile Glu 130                        150                        170
TCCACGCCGTTCAATGTCGCAGAGGGGAAGGAGGTGCTTCTACTTGTCCACAATCTGCCC
 Ser Thr Pro Phe Asn Val Ala Glu Gly Lys Glu Val Leu Leu Leu Val His Asn Leu Pro 190                        210                        230
CAGCATCTTTTTGGCTACAGCTGGTACAAAGGTGAAAGAGTGGATGGCAACCGTCAAATT
 Gln His Leu Phe Gly Tyr Ser Trp Tyr Lys Gly Glu Arg Val Asp Gly Asn Arg Gln Ile 250                        270                        290
ATAGGATATGTAATAGGAACTCAACAAGCTACCCCAGGGCCCGCATACAGTGGTCGAGAG
 Ile Gly Tyr Val Ile Gly Thr Gln Gln Ala Thr Pro Gly Pro Ala Tyr Ser Gly Arg Glu 310                        330                        350
ATAATATACCCCAATGCATCCCTGCTGATCCAGAACATCATCCAGAATGACACAGGATTC
 Ile Ile Tyr Pro Asn Ala Ser Leu Leu Ile Gln Asn Ile Ile Gln Asn Asp Thr Gly Phe 370                        390                        410
TACACCCTACACGTCATAAAGTCAGATCTTGTGAATGAAGAAGCAACTGGCCAGTTCCGG
 Tyr Thr Leu His Val Ile Lys Ser Asp Leu Val Asn Glu Glu Ala Thr Gly Gln Phe Arg
```

-continued

```
                430                          450                          470
GTATACCCGGAGCTGCCCAAGCCCTCCATCTCCAGCAACAACTCCAAACCCGTGGAGGAC
Val Tyr Pro Glu Leu Pro Lys Pro Ser Ile Ser Ser Asn Asn Ser Lys Pro Val Glu Asp 490                          510                          530
AAGGATGCTGTGGCCTTCACCTGTGAACCTGAGACTCAGGACGCAACCTACCTGTGGTGG
Lys Asp Ala Val Ala Phe Thr Cys Glu Pro Glu Thr Gln Asp Ala Thr Tyr Leu Trp Trp 550                          570                          590
GTAAACAATCAGAGCCTCCCGGTCAGTCCCAGGCTGCAGCTGTCCAATGGCAACAGGACC
Val Asn Asn Gln Ser Leu Pro Val Ser Pro Arg Leu Gln Leu Ser Asn Gly Asn Arg Thr 610                          630                          650
CTCACTCTATTCAATGTCACAAGAAATGACACAGCAAGCTACAAATGTGAAAACCAGAAC
Leu Thr Leu Phe Asn Val Thr Arg Asn Asp Thr Ala Ser Tyr Lys Cys Glu Thr Gln Asn 670                          690                          710
CCAGTGAGTGCCAGGCGCAGTGATTCAGTCATCCTGAATGTCCTCTATGGCCCGGATGCC
Pro Val Ser Ala Arg Arg Ser Asp Ser Val Ile Leu Asn Val Leu Tyr Gly Pro Asp Ala 730                          750                          770
CCCACCATTTCCCCTCTAAACACATCTTACAGATCAGGGGAAAATCTGAACCTCTCCTGC
Pro Thr Ile Ser Pro Leu Asn Thr Ser Tyr Arg Ser Gly Glu Asn Leu Asn Leu Ser Cys 790                          810                          830
CACGCAGCCTCTAACCCACCTGCACAGTACTCTTGGTTTGTCAATGGGACTTTCCAGCAA
His Ala Ala Ser Asn Pro Pro Ala Gln Tyr Ser Trp Phe Val Asn Gly Thr Phe Gln Gln 850                          870                          890
TCCACCCAAGAGCTCTTTATCCCCAACATCACTGTGAATAATAGTGGATCCTATACGTGC
Ser Thr Gln Glu Leu Phe Ile Pro Asn Ile Thr Val Asn Asn Ser Gly Ser Tyr Thr Cys 910                          930                          950
CAAGCCCATAACTCAGACACTGGCCTCAATAGGACCACAGTCACGACGATCACAGTCTAT
Gln Ala His Asn Ser Asp Thr Gly Leu Asn Arg Thr Thr Val Thr Thr Ile Thr Val Tyr 970                          990                         1010
GCAGAGCCACCCAAACCCTTCATCACCAGCAACAACTCCAACCCCGTGGAGGATGAGGAT
Ala Glu Pro Pro Lys Pro Phe Ile Thr Ser Asn Asn Ser Asn Pro Val Glu Asp Glu Asp 1030                         1050                         1070
GCTGTAGCCTTAACCTGTGAACCTGAGATTCAGAACACAACCTACCTGTGGTGGGTAAAT
Ala Val Ala Leu Thr Cys Glu Pro Glu Ile Gln Asn Thr Thr Tyr Leu Trp Trp Val Asn 1090                         1110                         1130
AATCAGAGCCTCCCGGTCAGTCCCAGGCTGCAGCTGTCCAATGACAACAGGACCCTCACT
Asn Gln Ser Leu Pro Val Ser Pro Arg Leu Gln Leu Ser Asn Asp Asn Arg Thr Leu Thr 1150                         1170                         1190
CTACTCAGTGTCACAAGGAATGATGTAGGACCCTATGAGTGTGGAATCCAGAACGAATTA
Leu Leu Ser Val Thr Arg Asn Asp Val Gly Pro Tyr Glu Cys Gly Ile Gln Asn Glu Leu 1210                         1230                         1250
AGTGTTGACCACAGCGACCCAGTCATCCTGAATGTCCTCTATGGCCCAGACGACCCCACC
Ser Val Asp His Ser Asp Pro Val Ile Leu Asn Val Leu Tyr Gly Pro Asp Asp Pro Thr 1270                         1290                         1310
ATTTCCCCCTCATACACCTATTACCGTCCAGGGGTGAACCTCAGCCTCTCCTGCCATGCA
Ile Ser Pro Ser Tyr Thr Tyr Tyr Arg Pro Gly Val Asn Leu Ser Leu Ser Cys His Ala 1330                         1350                         1370
GCCTCTAACCCACCTGCACAGTATTCTTGGCTGATTGATGGGAACATCCAGCAACACACA
Ala Ser Asn Pro Pro Ala Gln Tyr Ser Trp Leu Ile Asp Gly Asn Ile Gln Gln His Thr
```

```
                         1390                            1410                            1430

CAAGAGCTCTTTATCTCCAACATCACTGAGAAGAACAGCGGACTCTATACCTGCCAGGCC
Gln Glu Leu Phe Ile Ser Asn Ile Thr Glu Lys Asn Ser Gly Leu Tyr Thr Cys Gln Ala 1450                            1470                            1490

AATAACTCAGCCAGTGGCCACAGCAGGACTACAGTCAAGACAATCACAGTCTCTGCGGAG
Asn Asn Ser Ala Ser Gly His Ser Arg Thr Thr Val Lys Thr Ile Thr Val Ser Ala Glu 1510                            1530                            1550

CTGCCCAAGCCCTCCATCTCCAGCAACAACTCCAAACCCGTGGAGGACAAGGATGCTGTG
Leu Pro Lys Pro Ser Ile Ser Ser Asn Asn Ser Lys Pro Val Glu Asp Lys Asp Ala Val 1570                            1590                            1610

GCCTTCACCTGTGAACCTGAGGCTCAGAACACAACCTACCTGTGGTGGGTAAATGGTCAG
Ala Phe Thr Cys Glu Pro Glu Ala Gln Asn Thr Thr Tyr Leu Trp Trp Val Asn Gly Gln 1630                            1650                            1670

AGCCTCCCAGTCAGTCCCAGGCTGCAGCTGTCCAATGGCAACAGGACCCTCACTCTATTC
Ser Leu Pro Val Ser Pro Arg Leu Gln Leu Ser Asn Gly Asn Arg Thr Leu Thr Leu Phe 1690                            1710                            1730

AATGTCACAAGAAATGACGCAAGAGCCTATGTATGTGGAATCCAGAACTCAGTGAGTGCA
Asn Val Thr Arg Asn Asp Ala Arg Ala Tyr Val Cys Gly Ile Gln Asn Ser Val Ser Ala 1750                            1770                            1790

AACCGCAGTGACCCAGTCACCCTGGATGTCCTCTATGGGCCGGACACCCCCATCATTTCC
Asn Arg Ser Asp Pro Val Thr Leu Asp Val Leu Tyr Gly Pro Asp Thr Pro Ile Ile Ser 1810                            1830                            1850

CCCCCAGACTCGTCTTACCTTTCGGGAGCGAACCTCAACCTCTCCTGCCACTCGGCCTCT
Pro Pro Asp Ser Ser Tyr Leu Ser Gly Ala Asn Leu Asn Leu Ser Cys His Ser Ala Ser 1870                            1890                            1910

AACCCATCCCCGCAGTATTCTTGGCGTATCAATGGGATACCGCAGCAACACACACAAGTT
Asn Pro Ser Pro Gln Tyr Ser Trp Arg Ile Asn Gly Ile Pro Gln Gln His Thr Gln Val 1930                            1950                            1970

CTCTTTATCGCCAAAATCACGCCAAATAATAACGGGACCTATGCCTGTTTTGTCTCTAAC
Leu Phe Ile Ala Lys Ile Thr Pro Asn Asn Asn Gly Thr Tyr Ala Cys Phe Val Ser Asn 1990                            2010                            2030

TTGGCTACTGGCCGCAATAATTCCATAGTCAAGAGCATCACAGTCTCTGCATCTGGAACT
Leu Ala Thr Gly Arg Asn Asn Ser Ile Val Lys Ser Ile Thr Val Ser Ala Ser Gly Thr 2050                            2070                            2090

TCTCCTGGTCTCTCAGCTGGGGCCACTGTCGGCATCATGATTGGAGTGCTGGTTGGGGTT
Ser Pro Gly Leu Ser Ala Gly Ala Thr Val Gly Ile Met Ile Gly Val Leu Val Gly Val 2110                            2130                            2150

GCTCTGATATAGCAGCCCTGGTGTAGTTTCTTCATTTCAGGAAGACTGACAGTTGTTTTG
Ala Leu Ile End 2170                            2190                            2210

CTTCTTCCTTAAAGCATTTGCAACAGCTACAGTCTAAAATTGCTTCTTTACCAAGGATAT 2230                            2250                            2270

TTACAGAAAAGACTCTGACCAGAGATCGAGACCATCCTAGCCAACATCGTGAAACCCCAT 2290                            2310                            2330

CTCTACTAAAAATACAAAAATGAGCTGGGCTTGGTGGCGCGCACCTGTAGTCCCAGTTAC 2350                            2370                            2390

TCGGGAGGCTGAGGCAGGAGAATCGCTTGAACCCGGGAGGTGGAGATTGCAGTGAGCCCA
```

-continued

```
       2410                    2430                   2450
GATCGCACCACTGCACTCCAGTCTGGCAACAGAGCAAGACTCCATCTCAAA 2460      2470      2480       2490       2500
AAG AAA AGA AAA GAA GAC TCT GAC CTG TAC TCT TGA ATA CAA GTT TCT GAT ACC ACT 2510      2520      2530      2540      2550      2560
 GCA CTG TCT GAG AAT TTC CAA AAC TTT AAT GAA CTA ACT GAC AGC TTC ATG AAA CTG 2570      2580      2590      2600      2610      2620
TCC ACC AAG ATC AAG CAG AGA AAA TAA TTA AAT TCA TGG GGA CTA AAT GAA CTA ATG 2630      2640      2650      2660       2670      2680
AGG ATA ATA TTT TCA TAA TTT TTT ATT TGA AAT TTT GCT GAT TCT TTA AAT GTC TTG 2690      2700      2710      2720      2730
TTT CCC AGA TTT CAG GAA ACT TTT TTT CTT TTA AGC TAT CCA CTC TTA CAG CAA TTT 2740      2750      2760      2770      2780      2790
GAT AAA ATA TAG TTT TGT GAA CAA AAA TTG AGA CAT TTA CAT TTT ATC CCT ATG TGG 2800      2810      2820      2830
TCG CTC CAG ACT TGG GAA ACT ATT CAT GAA TAT TTA TAT TGT ATG
```

CEA-(c):

```
          10                  30                 50
CAGCCGTGCTCGAAGCGTTCCTGGAGCCCAAGCTCTCCTCCACAGGTGAAGACAGGGCCA 70                  90                110
GCAGGAGACACCATGGGGCACCTCTCAGCCCCACTTCACAGAGTGCGTGTACCCTGGCAG
             Met Gly His Leu Ser Ala Pro Leu His Arg Val Arg Val Pro Trp Gln 130                 150                170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                 210                230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                 270                290
AATCTGCCCCAGCAACTTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                 330                350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                 390                410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                 450                470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                 510                530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                 570                590
GTGGAGGACAAGGATGCTGTCGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr
```

-continued

```
          610                      630                      650
CTGTGGTGGATAAACAATCAGAGCCTCCCGGTCAGTCCCAGGCTGCAGCTGTCCAATGGC
Leu Trp Trp Ile  Asn Asn Gln Ser  Leu Pro Val Ser  Pro Arg Leu Gln  Leu Ser Asn Gly 670                      690                      710
AACAGGACCCTCACTCTACTCAGTGTCACAAGGAATGACACAGGACCCTATGAGTGTGAA
Asn Arg Thr Leu  Thr Leu Leu Ser  Val Thr Arg Asn  Asp Thr Gly Pro  Tyr Glu Cys Glu 730                      750                      770
ATACAGAACCCAGTGAGTGCGAACCGCAGTGACCCAGTCACCTTGAATGTCACCTATGGC
Ile Gln Asn Pro  Val Ser Ala Asn  Arg Ser Asp Pro  Val Thr Leu Asn  Val Thr Tyr Gly 790                      810                      830
CCGGACACCCCCACCATTTCCCCTTCAGACACCTATTACCGTCCAGGGGCAAACCTCAGC
Pro Asp Thr Pro  Thr Ile Ser Pro  Ser Asp Thr Tyr  Tyr Arg Pro Gly  Ala Asn Leu Ser 850                      870                      890
CTCTCCTGCTATGCAGCCTCTAACCCACCTGCACAGTACTCCTGGCTTATCAATGGAACA
Leu Ser Cys Tyr  Ala Ala Ser Asn  Pro Pro Ala Gln  Tyr Ser Trp Leu  Ile Asn Gly Thr 910                      930                      950
TTCCAGCAAAGCACACAAGAGCTCTTTATCCCTAACATCACTGTGAATAATAGTGGATCC
Phe Gln Gln Ser  Thr Gln Glu Leu  Phe Ile Pro Asn  Ile Thr Val Asn  Asn Ser Gly Ser 970                      990                      1010
TATACCTGCCACGCCAATAACTCAGTCACTGGCTGCAACAGG ACCACAGTCAAGACGATC
Tyr Thr Cys His  Ala Asn Asn Ser  Val Thr Gly Cys  Asn Arg  Thr Thr Val Lys Thr Ile 1030                     1050                     1070
ATAGTCACTGAGCTAAGTCCAGTAGTAGCAAAGCCCCAAATCAAAGCCAGCAAGACCACA
Ile Val Thr Glu  Leu Ser Pro Val  Val Ala Lys Pro  Gln Ile Lys Ala  Ser Lys Thr Thr 1090                     1110                     1130
GTCACAGGAGATAAGGACTCTGTGAACCTGACCTGCTCCACAAATGACACTGGAATCTCC
Val Thr Gly Asp  Lys Asp Ser Val  Asn Leu Thr Cys  Ser Thr Asn Asp  Thr Gly Ile Ser 1150                     1170                     1190
ATCCGTTGGTTCTTCAAAAACCAGAGTCTCCCGTCCTCGGAGAGGATGAAGCTGTCCCAG
Ile Arg Trp Phe  Phe Lys Asn Gln  Ser Leu Pro Ser  Ser Glu Arg Met  Lys Leu Ser Gln 1210                     1230                     1250
GGCAACACCACCCTCAGCATAAACCCTGTCAAGAGGGAGGATGCTGGGACGTATTGGTGT
Gly Asn Thr Thr  Leu Ser Ile Asn  Pro Val Lys Arg  Glu Asp Ala Gly  Thr Tyr Trp Cys 1270                     1290                     1310
GAGGTCTTCAACCCAATCAGTAAGAACCAAAGCGACCCCATCATGCTGAACGTAAACTAT
Glu Val Phe Asn  Pro Ile Ser Lys  Asn Gln Ser Asp  Pro Ile Met Leu  Asn Val Asn Tyr 1330                     1350                     1370
AATGCTCTACCACAAGAAAATGGCCTCTCACCTGGGGCCATTGCTGGCATTGTGATTGGA
Asn Ala Leu Pro  Gln Glu Asn Gly  Leu Ser Pro Gly  Ala Ile Ala Gly  Ile Val Ile Gly 1390                     1410                     1430
GTAGTGGCCCTGGTTGCTCTGATAGCAGTAGCCCTGGCATGTTTTCTGCATTTCGGGAAG
Val Val Ala Leu  Val Ala Leu Ile  Ala Val Ala Leu  Ala Cys Phe Leu  His Phe Gly Lys 1450                     1470                     1490
ACCGGCAGGGCAAGCGACCAGCGTGATCTCACAGAGCACAAACCCTCAGTCTCCAACCAC
Thr Gly Arg Ala  Ser Asp Gln Arg  Asp Leu Thr Glu  His Lys Pro Ser  Val Ser Asn His 1510                     1530                     1550
ACTCAGGACCACTCCAATGACCCACCTAACAAGATGAATGAAGTTACTTATTCTACCCTG
Thr Gln Asp His  Ser Asn Asp Pro  Pro Asn Lys Met  Asn Glu Val Thr  Tyr Ser Thr Leu
```

-continued

```
           1570                    1590                   1610
AACTTTGAAGCCCAGCAACCCACACAACCAACTTCAGCCTCCCCATCCCTAACAGCCACA
Asn Phe Glu Ala Gln Gln Pro Thr Gln Pro Thr Ser Ala Ser Pro Ser Leu Thr Ala Thr 1630                    1650                   1670
GAAATAATTTATTCAGAAGTAAAAAAGCAGTAATGAAACCTGTCCTGCTCACTGCAGTGC
Glu I.e Ile Tyr Ser Glu Val Lys Lys Gln 1690                    1710                   1730
TGATGTATTTCAAGTCTCTCACCCTCATCACTAGGAGATTCCTTTCCCCTGTAGGGTAGA 1750                    1770                   1790
GGGGTGGGGACAGAAACAACTTTCTCCTACTCTTCCTTCCTAATAGGCATCTCCAGGCTG 1810                    1830                   1850
CCTGGTCACTGCCCCTCTCTCAGTGTCAATAGATGAAAGTACATTGGGAGTCTGTAGGAA 1870                    1890                   1910
ACCCAACCTTCTTGTCATTGAAATTTGGCAAAGCTGACTTTGGGAAAGAGGGACCAGAAC 1930                    1950                   1970
TTCCCCTCCCTTCCCCTTTTCCCAACCTGGACTTGTTTTAAACTTGCCTGTTCAGAGCAC 1990                    2010                   2030
TCATTCCTTCCCACCCCCAGTCCTGTCCTATCACTCTAATTCGGATTTGCCATAGCCTTG 2050                    2070                   2090
AGGTTATGTCCTTTTCCATTAAGTACATGTGCCAGGAAACAGCGAGAGAGAGAAAGTAAA 2110                    2130                   2150
CGGCAGTAATGCTTCTCCTATTTCTCCAAAGCCTTGTGTGAACTAGCAAAGAGAAGAAAA 2170                    2190                   2210
TCAAATATATAACCAATAGTGAAATGCCACAGGTTTGTCCACTGTCAGGGTTGTCTACCT 2230                    2250                   2270
GTAGGATCAGGGTCTAAGCACCTTGGTGCTTAGCTAGAATACCACCTAATCCTTCTGGCA 2290                    2310                   2330
AGCCTGTCTTCAGAGAACCCACTAGAAGCAACTAGGAAAAATCACTTGCCAAAATCCAAG 2350                    2370                   2390
GCAATTCCTGATGGAAAATGCAAAAGCACATATATGTTTTAATATCTTTATGGGCTCTGT 2410                    2430                   2450
TCAAGGCAGTGCTGAGAGGGAGGGGTTATAGCTTCAGGAGGGAACCAGCTTCTGATAAAC 2470                    2490                   2510
ACAATCTGCTAGGAACTTGGGAAAGGAATCAGAGAGCTGCCCTTCAGCGATTATTTAAAT 2530                    2550                   2570
TGTTAAAGAATACACAATTTGGGGTATTGGGATTTTTCTCCTTTTCTCTGAGACATTCCA 2590                    2610                   2630
CCATTTTAATTTTTGTAACTGCTTATTTATGTGAAAAGGGTTATTTTTACTTAGCTTAGC 2650                    2670                   2690
TATGTCAGCCAATCCGATTGCCTTAGGTGAAAGAAACCACCGAAATCCCTCAGGTCCCTT 2710                    2730                   2750
GGTCAGGAGCCTCTCAAGATTTTTTTTGTCAGAGGCTCCAAATAGAAAATAAGAAAAGGT
```

-continued 2770  2790  2810
TTTCTTCATTCATGGCTAGAGCTAGATTTAACTCAGTTTCTAGGCACCTCAGACCAATCA 2830  2850  2870
TCAACTACCATTCTATTCCATGTTTGCACCTGTGCATTTTCTGTTTGCCCCCATTCACTT 2890  2910  2930
TGTCAGGAAACCTTGGCCTCTGCTAAGGTGTATTTGGTCCTTGAGAAGTGGGAGCACCCT 2950  2970  2990
ACAGGGACACTATCACTCATGCTGGTGGCATTGTTTACAGCTAGAAAGCTGCACTGGTGC 3010  3030  3050
TAATGCCCCTTGGGAAATGGGGCTGTGAGGAGGAGGATTATAACTTAGGCCTAGCCTCTT 3070  3090  3110
TTAACAGCCTCTGAAATTTTATCTTTTCTTCTATGGGGTCTATAAATGTATCTTATAATAA 3130  3150  3170
AAAGGAAGGACAGGAGGAAGACAGGCAAATGTACTTCTCACCCAGTCTTCTACACAGATG 3190  3210  3230
GAATCTCTTTGGGGCTAAGAGAAAGGTTTTATTCTATATTGCTTACCTGATCTCATGTTA 3250  3270  3290
GGCCTAAGAGGCTTTCTCCAGGAGGATTAGCTTGGAGTTCTCTATACTCAGGTACCTCTT 3310  3330  3350
TCAGGGTTTTCTAACCCTGACACGGACTGTGCATACTTTCCCTCATCCATGCTGTGCTGT 3370  3390  3410
GTTATTTAATTTTTCCTGGCTAAGATCATGTCTGAATTATGTATGAAAATTATTCTATGT 3430  3450
TTTTATAATAAAAATAATATATCAGACATCGAAAAAAAAAA CEA-(d):

10  30  50
CCGGGGGACACGCAGGGCCAACAGTCACAGCAGCCCTGACCAGAGCATTCCTGGAGCTCAAG 70  90  110
CTCTCTACAAAGAGGTGGACAGAGAAGACAGCAGAGACCATGGGACCCCCCTCAGCCCCT
                                                    Met Gly Pro Pro Ser Ala Pro 130  150  170
CCCTGCAGATTGCATGTCCCCTGGAAGGAGGTCCTGCTCACAGCCTCACTTCTAACCTTC
Pro Cys Arg Leu His Val Pro Trp Lys Glu Val Leu Leu Thr Ala Ser Leu Leu Thr Phe 190  210  230
TGGAACCCACCCACCACTGCCAAGCTCACTATTGAATCCACGCCATTCAATGTCGCAGAG
Trp Asn Pro Pro Thr Thr Ala Lys Leu Thr Ile Glu Ser Thr Pro Phe Asn Val Ala Glu 250  270  290
GGGAAGGAGGTTCTTCTACTCGCCCACAACCTGCCCCAGAATCGTATTGGTTACAGCTGG
Gly Lys Glu Val Leu Leu Leu Ala His Asn Leu Pro Gln Asn Arg Ile Gly Tyr Ser Trp 310  330  350
TACAAAGGCGAAAGAGTGGATGGCAACAGTCTAATTGTAGGATATGTAATAGGAACTCAA
Tyr Lys Gly Glu Arg Val Asp Gly Asn Ser Leu Ile Val Gly Tyr Val Ile Gly Thr Gln

-continued

```
        370                          390                          410
CAAGCTACCCCAGGGCCCGCATACAGTGGTCGAGAGACAATATACCCCAATGCATCCCTG
Gln Ala Thr Pro Gly Pro Ala Tyr Ser Gly Arg Glu Thr Ile Tyr Pro Asn Ala Ser Leu 430                          450                          470
CTGATCCAGAACGTCACCCAGAATGACACAGGATTCTACACCCTACAAGTCATAAAGTCA
Leu Ile Gln Asn Val Thr Gln Asn Asp Thr Gly Phe Tyr Thr Leu Gln Val Ile Lys Ser 490                          510                          530
GATCTTGTGAATGAAGAAGCAACCGGACAGTTCCATGTATACCCGGAGCTGCCCAAGCCC
Asp Leu Val Asn Glu Glu Ala Thr Gly Gln Phe His Val Tyr Pro Glu Leu Pro Lys Pro 550                          570                          590
TCCATCTCCAGCAACAACTCCAACCCCGTGGAGGACAAGGATGCTGTGGCCTTCACCTGT
Ser Ile Ser Ser Asn Asn Ser Asn Pro Val Glu Asp Lys Asp Ala Val Ala Phe Thr Cys 610                          630                          650
GAACCTGAGGTTCAGAACACAACCTACCTGTGGTGGGTAAATGGTCAGAGCCTCCCGGTC
Glu Pro Glu Val Gln Asn Thr Thr Tyr Leu Trp Trp Val Asn Gly Gln Ser Leu Pro Val 670                          690                          710
AGTCCCAGGCTGCAGCTGTCCAATGGCAACAGGACCCTCACTCTACTCAGCGTCAAAAGG
Ser Pro Arg Leu Gln Leu Ser Asn Gly Asn Arg Thr Leu Thr Leu Leu Ser Val Lys Arg 730                          750                          770
AACGATGCAGGATCGTATGAATGTGAAATACAGAACCCAGCGAGTGCCAACCGCAGTGAC
Asn Asp Ala Gly Ser Tyr Glu Cys Glu Ile Gln Asn Pro Ala Ser Ala Asn Arg Ser Asp 790                          810                          830
CCAGTCACCCTGAATGTCCTCTATGGCCCAGATGGCCCCACCATTTCCCCCTCAAAGGCC
Pro Val Thr Leu Asn Val Leu Tyr Gly Pro Asp Gly Pro Thr Ile Ser Pro Ser Lys Ala 850                          870                          890
AATTACCGTCCAGGGGAAAATCTGAACCTCTCCTGCCACGCAGCCTCTAACCCACCTGCA
Asn Tyr Arg Pro Gly Glu Asn Leu Asn Leu Ser Cys His Ala Ala Ser Asn Pro Pro Ala 910                          930                          950
CAGTACTCTTGGTTTATCAATGGGACGTTCCAGCAATCCACACAAGAGCTCTTTATCCCC
Gln Tyr Ser Trp Phe Ile Asn Gly Thr Phe Gln Gln Ser Thr Glu Glu Leu Phe Ile Pro 970                          990                          1010
AACATCACTGTGAATAATAGCGGATCCTATATGTGCCAAGCCCATAACTCAGCCACTGGC
Asn Ile Thr Val Asn Asn Ser Gly Ser Tyr Met Cys Gln Ala His Asn Ser Ala Thr Gly 1030                         1050                         1070
CTCAATAGGACCACAGTCACGATGATCACAGTCTCTGGAAGTGCTCCTGTCCTCTCAGCT
Leu Asn Arg Thr Thr Val Thr Met Ile Thr Val Ser Gly Ser Ala Pro Val Leu Ser Ala 1090                         1110                         1130
GTGGCCACCGTCGGCATCACGATTGGAGTGCTGGCCAGGGTGGCTCTGATATAGCAGCCC
Val Ala Thr Val Gly Ile Thr Ile Gly Val Leu Ala Arg Val Ala Leu Ile End 1150         1160         1170         1180         1190
TGG TGT ATT TTC GAT ATT TCA GGA AGA CTG GCA GAT TGG ACC AGA CCC TGA ATT CTT 1200         1210         1220         1230         1240         1250
  CTA GCT CCT CCA ATC CCA TTT TAT CCC ATG GAA CCA CTA AAA ACA AGG TCT GCT CTG 1260         1270         1280         1290         1300         1310
CTC CTG AAG CCC TAT ATG CTG GAG ATG GAC AAC TCA ATG AAA ATT TAA AGG AAA AAC 1320         1330         1340         1350         1360         1370
CCT CAG GCC TGA GGT GTG TGC CAC TCA GAG ACT TCA CCT AAC TAG AGA CAG GCA AAC
```

```
                1380        1390         1400         1410        1420

TGC AAA CCA nnC CTC TTT CGC TTG GCA GGA TGA TGG TGT CAT TAG TAT TTC ACA AGA 1430        1440         1450        1460         1470         1480

AGT AGC TTC AGA GGG TAA CTT AAC AGA GTA TCA GAT CTA TCT TGT CAA TCC CAA CGT 1490        1500        1510        1520        1530        1540

TTT ACA TAA AAT AAG CGA TCC TTT AGT GCA CCC AGT GAC TGA CAT TAG CAG CAT CTT 1550        1560        1570         1580        1590

TAA CAC AGC CGT GTG TTC AAG TGT ACA GTG GTC CTT TTC AGA GTT GGn nnT ACT CCA 1600        1610        1620        1630        1640        1650

ACT GAA ATG TTA AGG AAG AAG ATA GAT CCA ATT AAA AAA AAT TAA AAC CAA TTT AAA 1660        1670        1680        1690        1700        1710

AAA AAA AAA GAA CAC AGG AGA TTC CAG TCT ACT TGA GTT AGC ATA ATA CAG AAG TCC 1720        1730        1740        1750        1760

CCT CTA CTT TAA CTT TTA CAA AAA AGT AAC CTG AAC TAA TCT GAT GTT AAC CAA TGT 1770        1780        1790        1800        1810        1820

ATT TAT TTG TCT GGT TCT GTT TCC TTG TTC CAA TTT GAC AAA ACC CAC TGT TCT TGT 1830        1840        1850        1860        1870        1880

ATT GTA TTG CCC AGG GGG AGC TAT CAC TGT ACT TGT AGA GTG GTG CTG CTT TAA GTT 1890        1900        1910        1920        1930        1940

CAT AAA TCA CAA ATA AAA GCC AAT TAG CTC TAT AAC TAA AAA AAA AAA AAA AAA AAA 1950        1960

AAA AAA AAA AAA AAA AAA AAA AAA
```

A schematic relationship of the transmembrane CEA's, namely TM-1 (CEA-(c)), TM-2 (CEA-(e)), TM-3 (CEA-(f)) and TM-4 (CEA-(g)) is depicted in FIG. 1:

Assuming TM-1 is composed of five sections as depicted in FIG. 1, namely 10, 12, 14, 16 and 18, TM-2 differs from TM-1 in that the 100 amino acid (100 AA) section 14 is deleted and at splice point 20 between section 12 and 16, surprisingly an extra amino acid, namely Asp occurs.

TM-3 is the same as TM-1 except that section 18 is truncated at splice point 22, i.e., a section of 70 amino acids is deleted and results in a new section made up of subsections 24+26. Surprisingly, however, six new amino acids (section 26) occur. Another example of formation of a novel amino acid sequence resulting from a deletion of nucleic acid sequence is for platelet derived growth factor-A.

TM-4 is the same as TM-2 up until the end of subsection 24.

Subsection 24 is contained in section 18 of TM-1 and TM-2, but is not depicted in FIG. 1 for TM-1 and TM-2.

Some CEA epitopes are unique. These are the epitopes which have been useful for distinguishing the various CEA-like antigens immunologically. Peptide epitopes are defined by the linear amino acid sequence of the antigen and/or features resulting from protein folding. The information required for protein folding is encoded in the primary amino acid sequence. Therefore, antigenic differences ultimately result from differences in the primary structure of the different CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected for each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB89 and their derivatives, wider host range plasmids, e.g., RP4, and DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the 2 $\mu$ plasmid or derivatives thereof. Useful hosts may include bacterial hosts such as strains of *E. coli*, such as *E. coli* HB 101, *E. coli* X1776, *E. coli* X2282, *E. coli* MRC1 and strains of Pseudomonas, *Bacillus subtilis, Bacillus stearothermophilus* and other *E. coli*, bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the PstI site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoRI site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop condons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example, dA-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucleotides which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiecy with which those gene copies are transcibed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage $\lambda$ ($O_L P_L$ and $O_R P'_R$), the control region of Filamenteous single-stranded DNA phages, or other sequences which control the expression of genes of prokaryotic or eukaryotic cells and their viruses. Therefore, to improve the production of a particular polypeptide in an appropriate host, the gene coding for that polypeptide may be selected and removed from a recombinant nucleic acid molecule containing it and reinserted into a recombinant nucleic acid molecule closer or in a more appropriate relationship to its former expression control sequence or under the control of one of the above described expression control sequences. Such methods are known in the art.

As used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53–61 (1977) and N. E. Murray et al, "Molecular Cloning of the DNA Ligase Gene From Bacteriophage T4", *J. Mol. Biol.*, 132, pp. 493–505 (1979)) and the recombinant DNA molecule recircularized by incubation with DNA ligase. The desired recombinant phage is then selected as before and used to lysogenize a host strain of *E. coli*.

Particularly useful λ cloning vehicles contain a temperature-sensitive mutation in the repression gene cI and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those coded for by the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:
(1) the polypeptides expressed by the above described cells,
(2) polypeptides prepared by synthetic means,
(3) fragments of polypeptides (1) or (2) above, such fragments produced by synthesis of amino acids or by digestion or cleavage.

Regarding the synthetic peptides according to the invention, chemical synthesis of peptides is descibed in the following publications: S. B. H. Kent, *Biomedical Polymers*, eds. Goldberg, E. P. and Nakajima, A. (Academic Press, New York), 213–242, (1980); A. R. Mitchell, S. B. H. Kent, M. Engelhard and R. B. Merrifield, *J. Org. Chem.*, 43, 2845–2852, (1978); J. P. Tam, T.-W. Wong, M. Riemen, F.-S. Tjoeng and R. B. Merrifield, *Tet. Letters*, 4033–4036, (1979); S. Mojsov, A. R. Mitchell and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.), in press. 1981.

In the Merrifield solid phase procedure, the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by making for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysine) or other protecting groups commonly used in peptide synthesis;
(e) the activated amino acid is reacted with the peptide-resin for two hours at room temperature, resulting in addition of the new amino acid to the end of the growing peptide chain;
(f) the peptide-resin is washed with methylene chloride;
(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;
(h) the peptide-resin is washed with methylene chloride;
(i) steps (a) through (h) are repeated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites immediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide; asparaginyl-glycine bonds are cleaved by hydroxylamine.

The present invention has the following advantages:

(1) The nucleic acids coding for TM-1, TM-2 and TM-3 can be used as probes to isolate other members of the CEA gene family. (2) The nucleic acids coding for TM-1, TM-2 and TM-3 can be used to derive oligonucleotide probes to determine the expression of TM-1, TM-2, TM-3 and other CEA genes in various tumor types.

(3) TM-1, TM-2, TM-3 and TM-4 nucleotide sequences can be used to predict the primary amino acid sequence of the protein for production of synthetic peptides.

(4) Synthetic peptides derived from the above sequences can be used to produce sequence-specific antibodies.

(5) Immunoassays for each member of the CEA antigen family can be produced with these sequence-specific antibodies and synthetic peptides.

(6) The aforementioned immunoassays can be used as diagnostics for different types of cancer if it is determined that different members of the CEA family are clinically useful markers for different types of cancer.

Peptides according to the present invention can be labelled by conventional means using radioactive moieties (e.g., $^{125}$I), enzymes, dyes and fluorescent compounds, just to name a few.

Several possible configurations for immunoassays according to the present invention can be used. The readout systems capable of being employed in these assays are numerous and non-limiting examples of such systems include fluorescent and colorimetric enzyme systems, radioisotopic labelling and detection and chemiluminescent systems. Two examples of immunoassay methods are as follows:

(1) An enzyme linked immunoassay (ELISA) using an antibody preparation according to the present invention (including Fab or F(ab)' fragments derived therefrom) to a solid phase (such as a microtiter plate or latex beads) is attached a purified antibody of a specificity other than that which is conjugated to the enzyme. This solid phase antibody is contacted with the sample containing CEA antigen family members. After washing, the solid phase antibody-antigen complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of antigen in the sample.

(2) A competitive fluorometric immunoassay using fluorescently labelled peptide or synthetic peptides of the sequences for TM-2, TM-2, TM-3 and TM-4. In this example, the purified peptide expressed by cells or synthetic peptides thereof are fluorescently labelled. To a solid phase is attached a purified antibody. This solid phase is then contacted with sample containing CEA antigen family members to which has been added fluorescent peptide probe. After binding, excess probe is washed away the amount of bound probe is quantitated. The amount of bound fluorescent probe will be inversely proportional to the amount of antigen in the sample.

In the nucleic acid hybridization method according to the present invention, the nucleic acid probe is conjugated with a label, for example, an enzyme, a fluorophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods for these last two techniques are described by D. Gillespie and J. Bresser, "mRNA Immobilization in NaI: Quick Blots", *Biotechniques*, 184–192, November/December 1983 and J. Lawrence and R. Singer, "Intracellular Localization of Messenger RNAs for Cytosketal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The invention further provides a pharmaceutical composition containing as an active ingredient a complex of the invention in the form of a sterile and/or physiologically isotonic aqueous solution.

For parenteral administration, solutions and emulsions containing as an active ingredient the complex of the invention should be sterile and, if appropriate, blood-isotonic.

It is envisaged that the active complex will be administered perorally, parenterally (for example, intramuscularly, intraperitoneally, or intravenously), rectally or locally.

EXAMPLE 1

Preparation of cDNA in pcE22 which codes for TM2-CEA [CEA-(e)]

EXAMPLE 1a: RNA PREPARATION

Messenger RNA was prepared by the proteinase K extraction method of J. Favolaro, R. Treisman and R. Kamen, *Methods in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 µg of poly A+ RNA, approximately $3 \times 10^8$ cells of transfectant 23.411 (ATCC No. CRL 9731, deposited with the ATCC on Jun. 1, 1988), that expresses TM-1, TM-2, TM-3 and TM-4, Kamarck et al, *Proc. Natl. Acad. Sci., USA*, 84, 5350–5354, August 1987, were harvested from roller bottles after late logarithmic growth. Cells were lysed by homogenization in an ice-cold solution of 140 mM NaCl, 1.5 mM $MgCl_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centrifugation of the homogenate at $12,000 \times g$ for 20 minutes. The cytoplasmic fraction was mixed with an equal volume of 0.2M Tris-HCl, pH 7.8, 25 mM EDTA, 0.3M NaCl, 2% sodium dodecyl sulfate and 400 µg/ml of proteinase K, incubated for 1 hour at 37° C., then extracted once with an equal volume of phenol/cholorform (1:1/v:v) solution. Nucleic acids were obtained by ethanol precipitation of the separated aqueous phase. Total RNA was enriched by passage in 0.5M NaCl, 10 mM Tris-HCl, pH 7.8, 0.1% sarcosyl through an oligo dT (12–18) cellulose column. After washing, bound RNA wash eluted in the same solution without sodium chloride.

EXAMPLE 1b: REVERSE TRANSCRIPTION OF mRNA

Ten micrograms of poly A+ RNA were primed for reverse transcription with oligo dT (12–18) and pdN$_6$ primers. One hundred microliter reaction was performed for 4 hours at 42° C. with 200 units AMV reverse transcriptase (Life Science, Inc. St. Petersburg, Fla. U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

EXAMPLE 1c: CLONING OF pcE22 (PLASMID cDNA E22)

Synthetic DNA linkers

were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the 23.411 cell line, the size of the CEA-related mRNA was estimated at 3.6 kb. Therefore, cDNA fragments between 2 and 4 kb were recovered from gel slices and fragments were ethanol precipitated. After resuspension of cDNA in TE, EcoRI-cleaved lambda gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained after in vitro packaging and infection of *E. coli* host NM514.

EXAMPLE 1d: SCREENING OF RECOMBINANT LIBRARY

Five hundred thousand packaged lambda particles were plated on lawns of *E. coli* NM514 and replicate patterns were lifted onto nitrocellulose sheets as described by W. D. Benton and R. W. Davis, *Science* 196, 180–182, (1977). Positive phage were selected by hybridization with $^{32}$P-labeled LV7 cDNA insert probe that contained a domain repeated amoung various CEA family members. By multiple rounds of screening. Phage from individual plaques were amplified and titered, and these were used to prepare small quantities of recombinant phage DNA.

EXAMPLE 1e: DNA MANIPULATION

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci., U.S.A.*, 74, 5463–5467, (1977). The nucleic acid and translated sequence for cDNA in pcE22 is given hereinabove (TM-2 (CEA-(e)).

EXAMPLE 2

Preparation of cDNA in pcHT-6 which Partically Codes for TM3-CEA [CEA-(f)]

EXAMPLE 2a: RNA PREPARATION

Messenger RNA was prepared by the proteinase K extraction method of J. Favolaro, R. Treisman and R. Kamen, *Methods in Enzymology*, 65 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately 3×10$^8$ cells of HT-29 tumor cells (ATCC HTB38) were harvested from roller bottles after late logarithmic growth. Cells were lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centrifugation of the homogenate at 12,000×g for 20 minutes. The cytoplasmic fraction was mixed with an equal volume of 0.2M Tris-Hcl, pH 7.8, 25 mM EDTA, 0.3M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obtained by ethanol precipitation of the separated aqueous phase. Total RNA was enriched by passage in 0.5M NaCl, 10 mM Tris-HCl, pH 7.8, 0.1% sarcosyl through an oligo dT (12–18) cellulose column. After washing, bound RNA was eluted in the same solution without sodium chloride.

EXAMPLE 2b: REVERSE TRANSCRIPTION OF mRNA

Ten micrograms of HT-29 poly A+ RNA were primed for reverse transcription with oligo dT(12–18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

EXAMPLE 2c: CLONING OF pcHT-6 (PLASMID cDNA HT-6)

Synthetic DNA linkers

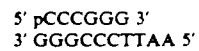

were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the HT-29 cell line, the size of the CEA-related mRNA was estimated at 2.2 kb. Therefore, cDNA fragments between 2 and 3 kb were recovered from gel slices and fragments were ethanol precipitated. After resuspension of cDNA in TE, EcoRI-cleaved lambda gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained after in vitro packaging and infection of E. coli host NM514.

EXAMPLE 2d: SCREENING OF RECOMBINANT LIBRARY

Five hundred thousand packaged lambda particles were plated on lawns of E. coli NM514 and replicate patterns were lifted onto nitrocellulose sheets as described by W. D. Benton and R. W. Davis, Science, 196, 180-182, (1977). Positive phage were selected by hybridization with $^{32}$P-labeled LV7 cDNA insert probe that contained a domain repeated among various CEA family members. By multiple rounds of screening, phage from individual plaques were amplified and titered, and these were used to prepare small quantities of recombinant phage DNA.

EXAMPLE 2e: DNA MANIPULATION

Phage DNA was prepared according to T. Maniatis, E. Fritsch and J. Sambrook, Molecular Cloning. A Laboratory Manual, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, Proc. Natl. Acad. Sci., U.S.A., 74, 5463-5467, (1977). The nucleic acid and translated sequence for cDNA in HT-6 not complete at the 5' end of its coding region, but the nucleotide sequence and restriction map of the HT-6 insert indicates that it is related to nucleic acid sequences of cDNA clones coding for CEA-(c) and CEA-(e). The nucleotide sequence of HT-6 insert differs from these clones at only nucleotide position 1463 to 1515 and 1676 to 2429 of the CEA-(c) cDNA. It is inferred from this result that the pcHT-6 insert is a partial coding sequence for CEA-(f) and the presumed nucleic acid and translated sequence of CEA-(f) is given hereinabove (TM-3 (CEA-(f)).

EXAMPLE 3

Preparation of cDNA which codes for TM4-CEA [CEA-(g)]

EXAMPLE 3a: RNA PREPARATION

Messenger RNA is prepared by the proteinase K extraction method of J. Favolaro, R. Treisman and R. Kamen, Methods in Enzymology, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 µg of poly A+ RNA, approximately $3 \times 10^8$ cells of transfectant 23.411 or tumor cell line HT-29 (ATCC HTB 38) are harvested from roller bottles after late logarithmic growth. Cells are lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei are separated by centrifugation of the homogenate at $12,000 \times g$ for 20 minutes. The cytoplasmic fraction is mixed with an equal volume of 0.2M Tris-Hcl, pH 7.8, 25 mM EDTA, 0.3M NaCl, 2% sodium dodecyl sulfate and 400 µg/ml of proteinase K, incubated for 1 hour at 37° C., then extracted once with an equal volume of phenol/-chloroform (1:1/v:v) solution. Nucleic acids are obtained by ethanol precipitation of the separated aqueous phase. Total RNA is enriched by passage in 0.5M NaCl, 10 mM Tris-HCl, pH 7.8, 0.1% sarcosyl through an oligo dT(12-18) cellulose column. After washing, bound RNA is eluted in the same solution without sodium chloride.

EXAMPLE 3b: REVERSE TRANSCRIPTION OF mRNA

Ten micrograms of 23.411 or HT 29 poly A+ RNA are primed for reverse transcription with oligo dT(12-18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids is replaced with the second complementary strand by treatment with RNase H, E. coli DNA polymerase I and E. coli DNA ligase at 12° C. and 22° C. for 1.5 hours each. Molecular ends are polished by treatment with T4 DNA polymerase. cDNA is phenol/chloroform extracted and purified over a "SEPHADEX G-50" spun column prepared in 10 mM Tris-HCl, pH 7.8, 1 mM EDTA (TE).

EXAMPLE 3c: CLONING OF cDNA FOR CEA-(g)

Synthetic DNA linkers

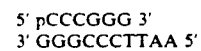

are attached to the ends of cDNA by blunt end ligation with excess T4 DNA ligase. Excess linkers are removed by chromatography through "SEPHADEX G-50" (medium) in TE, and by fractionation on 0.8% low melting agarose gel. Based on Northern blot analysis of poly A+RNA of the 23.411 and HT-29 cell lines, the size of the CEA-related mRNA is estimated at 1.7 kb. Therefore, cDNA fragments between 1 and 2 kb are recovered from gel slices and fragments are ethanol precipitated. After resuspension of cDNA in TE, EcoRI-cleaved lambda gt10 arms are added to cDNA at an estimated molar ratio of 1:1. Ligation proceeds at 7° C. for 2 days in the presence of T4 DNA ligase. Aliquots of the ligation reaction are added to commercially-obtained packaging mix (Stratagene, San Diego, Calif., U.S.A.). Phage particles are obtained after in vitro packaging and infection of E. coli host NM514.

EXAMPLE 3d: SCREENING OF RECOMBINANT LIBRARY

Five hundred thousand to one million packaged lambda particles are plated on lawns of E. coli NM514 and replicate patterns are lifted onto nitrocellulose sheets as described by W. D. Benton and R. W. Davis,

*Science*, 196, 180-182, (1977). Positive phage are selected by hybridization with ³²P-labeled LV7 cDNA insert probe that contained a domain repeated among various CEA family members. By this selection method, positive phage are obtained after multiple rounds of screening. Phage from individual plaques are amplified and titered, and these are used to prepare small quantities of recombinant phage DNA.

EXAMPLE 3e: DNA MANIPULATION

Phage DNA is prepared according to T. Maniatis, E. Fritsch and J. Sambrook, *Molecular Cloning. A Laboratory Manual*, Cold Spring Harbor, (1982). DNA segments are isolated from low melting agarose gels and inserted for subcloning into Bluescript plasmid vectors (Stratagene, San Diego, Calif., U.S.A.). DNA sequencing is performed by the dideoxy termination method of F. Sanger, S. Nicklen and A. Coulson, *Proc. Natl. Acad. Sci., U.S.A.*, 74, 5463-5467, (1977). The nucleotide and translated sequence for a cDNA coding for CEA-(g) is given hereinabove (TM-4 (CEA-(g)).

EXAMPLE 4

Screening of a KG-1 cDNA Library with ³²P-labelled CEA Probe, LV7 (CEA-(A))

A segment of cDNA coding for a portion of carcinoembryonic antigen [LV7 or CEA-(a)] was radiolabelled by random priming and used to detect homologous sequences on filter replicas of a commercial cDNA library prepared from KG-1 cells in bacteriophage vector λ gt11 (Clontech Laboratories, Inc., Palo Alto, Calif., U.S.A.). Hybridizations were performed at 68° C. in 2×SSSPE (1×SSPE—0.15M NaCl, 0.01M sodium phosphate and 1 mM EDTA, pH 7), 5×Denhardt's solution and 100 μg of denatured salmon sperm DNA per ml, and post-hybridization washes were in 0.2×SSC, 0.25% sodium dodecyl sulfate.

Positive phage were picked, rescreened to homogeneity, and amplified for production of DNA. cDNA inserts were excised from phage DNA with EcoRI endonuclease and subcloned into the EcoRI site of the plasmid vector pBluescript KS. DNA sequencing on double-stranded DNA was by the method of Sanger et al, supra. The sequences of two different inserts from the KG-1 cDNA library are shown below:

```
pcKGCEA1:
  1  acagcacagctgacagccgtactcaggaagcttctggatcctaggcttatctccacagag                          60

61  gagaacacacaagcagcagagaccatg gggcccctc tca gcccct ccctgc aca cacctc                   120
                                MetGlyProLeuSerAlaProProCysThrHisLeu 121  atcact tgg aag ggggtc ctg ctc aca gcatcactt tta aac ttc tgg aat ccgcccaca            180
     IleThrTrpLysGlyValLeuLeuThrAlaSerLeuLeuAsnPheTrpAsnProProThr 181  act gcccaa gtc acg att gaa gcccag cca ccc aaa gtt tct gag gggaag gat gtt ctt         240
     ThrAlaGlnValThrIleGluAlaGlnProProLysValSerGluGlyLysAspValLeu 241  cta ctt gtc cacaat ttg ccc cag aat ctt gct ggctac att tgg tac aaa gggcaa atg         300
     LeuLeuValHisAsnLeuProGlnAsnLeuAlaGlyTyrIleTrpTyrLysGlyGlnMet 301  aca tac gtc tac cat tac att aca tca tat gta gta gac ggt caa aga att atatat ggg       360
     ThrTyrValTyrHisTyrIleThrSerTyrValValAspGlyGlnArgIleIleTyrGly 361  cct gcatac agt gga aga gaa aga gta tat tcc aat gcatcc ctg atccag aat gtc             420
     ProAlaTyrSerGlyArgGlyArgValTyrSerAsnAlaSerLeuLeuIleGlnAsnVal 421  acg cag gag gat gcagga tcc tac acc tta cacatcataaag cga cgc gat gggact gga           480
     ThrGlnGluAspAlaGlySerTyrThrLeuHisIleIleLysArgArgAspGlyThrGly 481  gga gta act gga cat ttc acc ttc acc tta cacctg gagact cccaag ccc tcc atctcc          540
     GlyValThrGlyHisPheThrPheThrLeuHisLeuGlyThrProLysProSerIleSer 541  agcagcaac tta aat cccagg gag gccatg gag gct gtg atctta acc tgt gat cct gcg           600
     SerSerAsnLeuAsnProArgGluAlaMetGluAlaValIleLeuThrCysAspProAla 601  act cca gccgcaagctac cag tgg tgg atg aat ggt cag agcctc cct atg act cacagg           660
     ThrProAlaAlaSerTyrGlnTrpTrpMetAsnGlyGlnSerLeuProMetThrHisArg 661  ttg cag ctg tcc aaa acc aac agg acc ctc ttt atattt ggt gtc aca aag tat att gca       720
     LeuGlnLeuSerLysThrAsnArgThrLeuPheIlePheGlyValThrLysTyrIleAla 721  gga ccc tat gaa tgt gaa atacgg aac cca gtg agt gccagccgc agt gac cca gtc acc         780
     GlyProTyrGluCysGluIleArgAsnProValSerAlaSerArgSerAspProValThr 781  ctg aat ctc ctc cca aag ctg tcc aag ccc tac atcaca atcaac aac tta aac cccaga         840
     LeuAsnLeuLeuProLysLeuSerLysProTyrIleThrIleAsnAsnLeuAsnProArg 841  gag aat aag gat gtc tta acc ttc acc tgt gaa cct aag agt gag aac tac acc tac att     900
     GluAsnLysAspValLeuThrPheThrCysGluProLysSerGluAsnTyrThrTyrIle 901  tgg tgg cta aat ggt cag agcctc cct gtc agt cccagg gta aag cga cccatt gaa aac         960
     TrpTrpLeuAsnGlyGlnSerLeuProValSerProArgValLysArgProIleGluAsn 961  agg atcctc att cta cccaat gtc acg aga aat gaa aca gga cct tat caa tgt gaa ata        1020
     ArgIleLeuIleLeuProAsnValThrArgAsnGluThrGlyProTyrGlnCysGluIle
```

-continued

| | | |
|---|---|---|
| 1021 | cgg gac cga tat ggt ggc atccgc agt gac cca gtc acc ctg aat gtc ctc tat ggt cca<br>ArgAspArgTyrGlyGlyIleArgSerAspProValThrLeuAsnValLeuTyrGlyPro | 1080 |
| 1081 | gac ctc ccc agcatt tac cct tca ttc acc tat tac cgt tca gga gaa aac ctc tac ttt<br>AspLeuProSerIleTyrProSerPheThrTyrTyrArgSerGlyGluAsnLeuTyrPhe | 1140 |
| 1141 | tcc tgc ttc ggt gag tct aac cca cgg gca caa tat tct tgg aca att aat gggaag ttt<br>SerCysPheGlyGluSerAsnProArgAlaGlnTyrSerTrpThrIleAsnGlyLysPhe | 1200 |
| 1201 | cag cta tca gga caa aag ctc tct atccccc caa ataact aca aag cat agt gggctc tat<br>GlnLeuSerGlyGlnLysLeuSerIleProGlnIleThrThrLysHisSerGlyLeuTyr | 1260 |
| 1261 | gct tgc tct gtt cgt aac tca gccact ggc aag gaa agctcc aaa tcc atcaca gtc aaa<br>AlaCysSerValArgAsnSerAlaThrGlyLysGluSerSerLysSerIleThrValLys | 1320 |
| 1321 | gtc tct gac tgg atatta ccctgaattctactagttcctccaattccatttctcccatg<br>ValSerAspTrpIleLeuProEnd | 1380 |
| 1381 | gaatcacgaagagcaagacccactctgttccagaagccctataatctggaggtggacaac | 1440 |
| 1441 | tcgatgtaaatttcatgggaaaaccctttgtacctgacatgtgagccactcagaactcacc | 1500 |
| 1501 | aaaatgttcgacaccataacaacagctactcaaactgtaaaccaggataagaagttgatg | 1560 |
| 1561 | acttcacactgtggacagttttcaaagatgtcataacaagactccccatcatgacaagg | 1620 |
| 1621 | ctccaccctctactgtctgctcatgcctgcctcttcacttggcaggataatgcagtcat | 1680 |
| 1681 | tagaatttcacatgtagtagcttctgagggtaacaacagagtgtcagatatgtcatctca | 1740 |
| 1741 | acctcaaacttttacgtaacatctcagggaaatgtggctctctccatcttgcatacaggg | 1800 |
| 1801 | ctcccaatagaaatgaacacagagatattgcctgtgtgtttgcagagaagatggtttcta | 1860 |
| 1861 | taaagagtaggaaagctgaaattatagtagagtctcctttaaatgcacattgtgtggatg | 1920 |
| 1921 | gctctcaccatttcctaagagatacagtgtaaaaacgtgacagtaatactgattctagca | 1980 |
| 1981 | gaataaacatgtaccacatttgcaaaaaa | 2010 | pcKGCEA2.

| | | |
|---|---|---|
| 1 | gggtggatcctaggctcatctccataggggagaacacacatacagcagagaccatg gga<br>                                                                          MetGly | 59 |
| 60 | ccc ctc tca gcccct ccc tgc act cag cacatcacc tgg aag gggctc ctg ctc aca gca<br>ProLeuSerAlaProProCysThrGlnHisIleThrTrpLysGlyLeuLeuLeuThrAla | 119 |
| 120 | tca ctt tta aac ttc tgg aac ctg ccc acc act gcccaa gta ataatt gaa gcccag cca<br>SerLeuLeuAsnPheTrpAsnLeuProThrThrAlaGlnValIleIleGluAlaGlnPro | 179 |
| 180 | ccc aaa gtt tct gag gggaag gat gtt ctt cta ctt gtc cacaat ttg ccc cag aat ctt<br>ProLysValSerGluGlyLysAspValLeuLeuLeuValHisAsnLeuProGlnAsnLeu | 239 |
| 240 | act ggc tac atctgg tac aaa gggcaa atg acg gac ctc tac cat tac att aca tca tat<br>ThrGlyTyrIleTrpTyrLysGlyGlnMetThrAspLeuTyrHisTyrIleThrSerTyr | 299 |
| 300 | gta gta gac ggt caa att atatat gggcct gcctac agt ggacga gaa aca gta tat tcc<br>ValValAspGlyGlnIleIleTyrGlyProAlaTyrSerGlyArgGluThrValTyrSer | 359 |
| 360 | aat gcatcc ctg ctg atccag aat gtc aca cag gag gat gcaggatcctac acc tta cac<br>AsnAlaSerLeuLeuIleGlnAsnValThrGlnGluAspAlaGlySerTyrThrLeuHis | 419 |
| 420 | atcataaag cga ggc gat gggact gga gga gta act ggatat ttc act gtc acc tta tac<br>IleIleLysArgGlyAspGlyThrGlyGlyValThrGlyTyrPheThrValThrLeuTyr | 479 |
| 480 | tcg gagact ccc aag cgc tcc atctcc agcagcaac tta aac ccc agg gag gtc atg gag<br>SerGluThrProLysArgSerIleSerSerSerAsnLeuAsnProArgGluValMetGlu | 539 |
| 540 | gct gtg cgc tta atctgt gat cct gagact ccggat gcaagctac ctg tgg ttg ctg aat<br>AlaValArgLeuIleCysAspProGluThrProAspAlaSerTyrLeuTrpLeuLeuAsn | 599 |
| 600 | ggt cag aac ctc cct atg act cacagg ttg cag ctg tcc aaa acc aac agg acc ctc tat<br>GlyGlnAsnLeuProMetThrHisArgLeuGlnLeuSerLysThrAsnArgThrLeuTyr | 659 |
| 660 | cta ttt ggt gtc aca aag tat att gcagggccc tat gaa tgt gaa atacgg agg gga gtg<br>LeuPheGlyValThrLysTyrIleAlaGlyProTyrGluCysGluIleArgArgGlyVal | 719 |
| 720 | agt gccagccgc agt gac cca gtc acc ctg aat ctc ctc ccgaagctg cccatg cct tac<br>SerAlaSerArgSerAspProValThrLeuAsnLeuLeuProLysLeuProMetProTyr | 779 |
| 780 | atcacc atcaac aac tta aac cccagg gagaag aag gat gtg tta gccttc acc tgt gaa<br>IleThrIleAsnAsnLeuAsnProArgGluLysLysAspValLeuAlaPheThrCysGlu | 839 |

| | | |
|---|---|---|
| 840 | cct aag agt cgg aac tac acc tac att tgg tgg cta aat ggt cag agcctc ccggtc agt<br>ProLysSerArgAsnTyrThrTyrIleTrpTrpLeuAsnGlyGlnSerLeuProValSer | 899 |
| 900 | ccgagg gta aag cga ccc att gaa aac agg atactc att cta ccc agt gtc acg aga aat<br>ProArgValLysArgProIleGluAsnArgIleLeuIleLeuProSerValThrArgAsn | 959 |
| 960 | gaa aca gga ccc tat caa tgt gaa atacgg gac cga tat ggt ggc atccgc agt aac cca<br>GluThrGlyProTyrGlnCysGluIleArgAspArgTyrGlyGlyIleArgSerAsnPro | 1019 |
| 1020 | gtc acc ctg aat gtc ctc tat ggt cca gac ctc ccc aga att tac cct tac ttc acc tat<br>ValThrLeuAsnValLeuTyrGlyProAspLeuProArgIleTyrProTyrPheThrTyr | 1079 |
| 1080 | tac cgt tca gga gaa aac ctc gac ttg tcc tgc ttt gcggac tct aac cca ccg gca gag<br>TyrArgSerGlyGluAsnLeuAspLeuSerCysPheAlaAspSerAsnProProAlaGlu | 1139 |
| 1140 | tat ttt tgg aca att aat ggg aag ttt cag cta tca gga caa aag ctc ttt atccccaa<br>TyrPheTrpThrIleAsnGlyLysPheGlnLeuSerGlyGlnLysLeuPheIleProGln | 1199 |
| 1200 | att act aca aat cat agcgggctc tat gct tgc tct gtt cgt aac tca gccact ggc aag<br>IleThrThrAsnHisSerGlyLeuTyrAlaCysSerValArgAsnSerAlaThrGlyLys | 1259 |
| 1260 | gaa atctcc aaa tcc atg atagtc aaa gtc tct ggt ccc tgc cat gga aac cag aca gag<br>GluIleSerLysSerMetIleValLysValSerGlyProCysHisGlyAsnGlnThrGlu | 1319 |
| 1320 | tct cat taatggctgccacaatagagacactgagaaaaagaacaggttgataccttcatg<br>SerHisEnd | 1379 |
| 1380 | aaattcaagacaaagaagaaaaaggctcaatgttattggactaaataatcaaaaggataa | 1439 |
| 1440 | tgttttcataatttttattggaaaatgtgctgattcttggaatgttttattctccagatt | 1499 |
| 1500 | tatgaacttttttcttcagcaattggtaaagtatactttgtaaacaaaaattgaaaca | 1559 |
| 1560 | tttgcttttgctctctatctgagtgcccccc | 1591 |

It will be appreciated that the instant specification and claims are set forth by way of illustration and not limitation and that various modifications and changes may be made without departing from the spirit and scope of the present invention.

What is claimed is:

1. An isolated nucleic acid sequence which codes for a polypeptide belonging to the CEA family, selected from the sequences listed below:
   TM-2
   TM-3
   KGCEA1
   KGCEA2.

2. A replicable recombinant cloning vehicle having an insert comprising a nucleic acid according to claim 1.

3. An isolated nucleic acid sequence which codes for a polypeptide belonging to the CEA family, comprising TM-2.

4. An isolated nucleic acid sequence which codes for a polypeptide belonging to the CEA family, comprising TM-3.

5. An isolated nucleic acid sequence which codes for a polypeptide belonging to the CEA family, comprising KGCEA1.

6. An isolated nucleic acid sequence which codes for a polypeptide belonging to the CEA family, comprising KGCEA2.

* * * * *